United States Patent
Venugopal et al.

(10) Patent No.: US 9,546,200 B2
(45) Date of Patent: Jan. 17, 2017

(54) PEPTIDE FOR PROTECTION OF ALLERGIC RESPIRATORY DISORDERS

(75) Inventors: Changaram S. Venugopal, Prairieville, LA (US); Sudhirdas K. Prayaga, Dardenne Prairie, MO (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 14/124,297

(22) PCT Filed: Jun. 8, 2012

(86) PCT No.: PCT/US2012/041592
§ 371 (c)(1),
(2), (4) Date: Dec. 6, 2013

(87) PCT Pub. No.: WO2012/170842
PCT Pub. Date: Dec. 13, 2012

(65) Prior Publication Data
US 2014/0105906 A1   Apr. 17, 2014

Related U.S. Application Data

(60) Provisional application No. 61/494,948, filed on Jun. 9, 2011.

(51) Int. Cl.
| | |
|---|---|
| *G01N 33/53* | (2006.01) |
| *A61K 39/00* | (2006.01) |
| *A61K 39/385* | (2006.01) |
| *A61K 38/00* | (2006.01) |
| *A61K 38/04* | (2006.01) |
| *C07K 7/00* | (2006.01) |
| *C07K 16/00* | (2006.01) |
| *C07K 17/00* | (2006.01) |
| *C07K 14/47* | (2006.01) |
| *G01N 33/68* | (2006.01) |
| *C07K 16/18* | (2006.01) |

(52) U.S. Cl.
CPC .......... *C07K 14/47* (2013.01); *A61K 39/0005* (2013.01); *C07K 16/18* (2013.01); *G01N 33/6854* (2013.01); *G01N 33/6893* (2013.01); *A61K 38/00* (2013.01); *A61K 2039/505* (2013.01); *A61K 2039/552* (2013.01); *A61K 2039/55566* (2013.01); *A61K 2039/577* (2013.01); *A61K 2039/6081* (2013.01); *C07K 2317/33* (2013.01); *C07K 2317/34* (2013.01); *G01N 2800/122* (2013.01)

(58) Field of Classification Search
None
See application file for complete search history.

(56) References Cited

U.S. PATENT DOCUMENTS

| | | | |
|---|---|---|---|
| 6,255,281 B1 | 7/2001 | Pilon et al. | 514/12 |
| 7,846,899 B2 | 12/2010 | Pilon | 514/12 |
| 2005/0261180 A1 | 11/2005 | Pilon et al. | 514/12 |
| 2009/0324575 A1* | 12/2009 | Shayman et al. | 424/94.6 |
| 2011/0240012 A1 | 10/2011 | Pilon | 128/200.14 |

OTHER PUBLICATIONS

Muller-Schottle et al. 'Full-Length Complementary DNA and the Derived Amino Acid Sequence of Horse Uteroglobin.' Biol. Reprod. 66:1723-1728, 2002.*
Ngo et al., In the Protein Folding Problem and Tertiary Structure Prediction, Merz, et al., (ed.), Birkhauser, Boston, MA, pp. 433 and 492495 (1994).*
Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysinc Residue," The Journal of Cell Biology, vol. 111:2129-2138 (1990).*
Lazar, Eliane et al., "Transforming Growth Factor alpha: Mutation of Aspartic Acid 47 and Leucine 48 Results in Different Biological Activities," Molecular and Cellular Biology, vol. 8(3): 1247-1252 (1988).*
Skolnick, Jeffrey et al., "From genes to protein structure and function: novel applications of computational approaches in the genomic era," Trends in Biotech., vol. 18:34-39 (2000).*
Attwood, Teresa K., "The Babel of Bioinforrnatics," Science, vol. 290(5491):471-473 (2000).*
Kuby Immunology, 4th Edition, Chapter 18, "Vaccines," pp. 449-465 (2001).*
Harlow et al. 'Antibodies A laboratory manual.' Cold Spring Harbor, New York. Cold Spring Harbor Press: 53-137, 1988.*
Cote et al. 'Multiple secretoglobin 1A1 genes are differentially expressed in horses.' BMC Genomic 13:712, 2012.*
Cote et al. 'Phylogenetic relationships among Perissodactyla: Secretoglobin 1A1 gene duplication and triplication in the Equidae family.' Molec. Phlyogen. Evol. 69:430-436, 2013.*
Mukherjee et al. 'Allergiuc Asthma: INfluence of Genetic and Environmentla Factors.' J. Biol. Chem. 286(38):32883-32889, 2011.*
Ainsworth, D. M. et al., "IgG antibody responses to an inhaled antigen in horses with "heaves" (recurrent airway obstruction)," Vet Immunol. Immunopathol., vol. 84, iss. 3-4, pp. 169-180 (Jan. 15, 2002).
Barnes, P.J. et al., "Inflammatory mediators of asthma," Pharmacol. Rev., vol. 40, No. 1, pp. 49-84 (1988).
Beadle, R.E., "Summer pasture-associated obstructive pulmonary disease. In: Robinson N.E., ed. Current therapy in equine medicine," Philadelphia: W.B. Saunders Co., pp. 512-516 (1983).

(Continued)

*Primary Examiner* — Nora Rooney
(74) *Attorney, Agent, or Firm* — Venable LLP; Keith G. Haddaway; Miguel A. Lopez

(57) ABSTRACT

A peptide (Peptide-1) based on the C-terminal of Equine CC10 has been discovered that can be used as a vaccine to protect horses from respiratory airway obstruction (RAO). Antibodies to Peptide-1 may also be administered for short-term passive immunotherapy to RAO-affected horses, and can be used to measure the level of CC10 protein in serum to identify potential RAO horses (horses with reduced CC10). Due to similarities between equine RAO and human asthma, this peptide or its antibodies may also be useful in treatment or prevention of human asthma.

17 Claims, 6 Drawing Sheets

(56) References Cited

OTHER PUBLICATIONS

Bochner, B.S. et al., "Allergy and Asthma," J. Allergy Clin. Immunol., vol. 115, No. 5, pp. 953-959 (2005).

Bowles K.S. et al., "A novel model for equine recurrent airway obstruction," Vet. Immunol. Immunopathol., vol. 87, No. 3-4, pp. 385-389 (2002).

Buechner-Maxwell, V., "Airway hyperresponsiveness. Equine respiratory disorders. The Compendium," vol. 15, pp. 1379-1389 (1993).

Bureau, F. et al., "Mechanism of persistent NF-Kappa B activity in the bronchi of an animal model of human asthma," J. Immunol., vol. 165, No. 10, pp. 5822-5830 (2000).

Carlsson H.E. et al., "Titration of antibodies to Salmonella O. antigens by enzyme-linked immunosorbent assay," Infect. Immun., vol. 6, No. 5, pp. 703-708 (1972).

Derksen F.J. et al., "Overview of the equine respiratory system. In: Equine Respiratory Diseases," Ed. Lekeux P., International Veterinary Information Service (www.ivis.org), Ithaca, New York, USA (2002).

Drazen, J.M., "Physiologic basis and interpretation of common indices of respiratory mechanical function," Environ. Health Prespective, vol. 16, pp. 11-16 (1976).

Drazen, J.M. et al., "Animal models of asthma and chronic bronchitis," Clin. Experiment Allergy, vol. 29, pp. 37-47 (1999).

Drazen, J.M. et al., "H2 receptor mediated inhibition of immediate type hypersensitivity reactions in vivo," Am. Rev. Respir. Dis., vol. 117, pp. 479-484 (1978).

Drazen, J.M. et al., "Mouse models of airway responsiveness," In: Annual Review of Physiology, Hoffman J.F., De Weer P. (eds), Annual Reviews, Inc., California, vol. 61, pp. 593-625 (1999).

Harada, M. et al., "IL-21-induced Bepsilon cell apoptosis mediated by natural killer T cells suppresses IgE responses," J. Exp. Med., vol. 203, No. 13, pp. 2929-2937 (2006).

Hargreave, F.E. et al., "The origin of airway hyperresponsiveness," J. Allergy. Clin. Immunol., vol. 78, pp. 825-829 (1986).

Hart, L.A., pp. Activation and localization of transcription factor, nuclear factor Kappa B, in asthma, Am. Rev. Respir. Crit. Care Med., vol. 158, pp. 1585-1590 (1998).

Horohov, D.W. et al., "Temporal regulation of cytokine mRNA expression in equine recurrent airway obstruction," vol. 108, Nos. 1-2, pp. 237-245 (2005).

Johansson, S. et al., "CC16 inhibits the migration of eosinophils towards the formyl peptide fMLF but not towards PGD2," Inflammation, vol. 32, No. 2, pp. 65-69 (2009).

Katavolos, P. et al., "Clara Cell Secretary Protein Is Reduced in Equine Recurrent Airway Obstruction," Vet. Pathol., vol. 46, pp. 604-613 (2009).

Krishnakumar, S. et al., "Non-adrenergic,non-cholinergic excitatory innervation in asthma: Role of neurokinin-2 receptors," J. Auton. & Autacoid. Pharmacol., vol. 22, pp. 1-11 (2002).

Lee, H.A. et al., "Isotype and IgG subclass distribution of autoantibody response to alpha-enolase protein in adult patients with severe asthma," Yonsei Med. J., vol. 49, No. 6, pp. 923-930 (2008).

McGinnis, S. et al., "BLAST: at the core of a powerful and diverse set of sequence analysis tools," Nucleic Acids Res., vol. 32 (Web Server issue), pp. W20-W25 (2004).

Morán, G. et al., "Detection of reaginic antibodies against Faenia rectivirgula from the serum of horses affected with Recurrent Airway Obstruction by an in vitro bioassay," Vet. Res. Commun., vol. 34, No. 8, pp. 719-726 (2010).

Radon, K., "The two sides of the 'Endotoxin Coin'," Occup. Environ. Med., vol. 63, pp. 73-78 (2006).

Roy, S.R., "Asthma," South. Med. J., vol. 96, No. 11, pp. 1061-1067 (2003).

Schmitz, N. et al., "Displaying Fel. d1 on virus-like particles prevents reactogenicity despite greatly enhanced immunogenicity: a novel therapy for cat allergy," J. Exp. Med., vol. 206, No. 9, pp. 1941-1955 (2009).

Seahorn, T.L. et al., "Quantification of antigen-specific antibody concentrations in tracheal lavage fluid of horses with summer pasture-associated obstructive pulmonary disease," Am. J. Vet. Res., vol. 58, pp. 1408-1411 (1997).

Snapper, J.R., "Large animal models of asthma," Am. Rev. Respir. Dis., vol. 133, pp. 351-352, (1986).

Venugopal, C.S. et al., "Transcriptional changes associated with equine recurrent airway obstruction in affected and unaffected horses," Am. J. Vet. Res., vol. 71, No. 4, pp. 476-482 (2010).

Westritschnig, K. et al., "A hypoallergenic vaccine obtained by tail-to-head restructuring of timothy grass pollen profilin, Phl p 12, for the treatment of cross-sensitization to profilin," J Immunol., vol. 179, No. 11, pp. 7624-7634 (2007).

YuXia, C. et al., "Functional Expression of IgG-Fc Receptors in Human Airway Smooth Muscle Cells," Am. J. Respir. Cell and Mol. Biol., vol. 44, No. 5, pp. 665-672 (2011).

* cited by examiner

SEQUENCE LISTING

```
<160> NUMBER OF SEQ ID NOS: 2

<210> SEQ ID NO 1
<211> LENGTH: 21
<212> TYPE: PRT
<213> ORGANISM: Artificial sequence
<220> FEATURE:
<223> OTHER INFORMATION: Artificial peptide

<400> SEQUENCE: 1

Lys Asn Thr Lys Asp Ser Ile Leu Lys Leu Met Asp Lys Ile Ala Lys
1               5                   10                  15

Ser Pro Leu Cys Ala
            20

<210> SEQ ID NO 2
<211> LENGTH: 20
<212> TYPE: PRT
<213> ORGANISM: Artificial sequence
<220> FEATURE:
<223> OTHER INFORMATION: Synthetic peptide

<400> SEQUENCE: 2

Glu Pro Ser Lys Pro Asp Ala Asp Met Lys Ala Ala Thr Thr Gln Leu
1               5                   10                  15

Lys Thr Leu Val
            20
```

PEPTIDE FOR PROTECTION OF ALLERGIC RESPIRATORY DISORDERS

This is the United States national stage of international application PCT/US2012/041592, international filing date 8 Jun. 2012, which claims the benefit of the filing date of provisional U.S. application Ser. No. 61/494,948, filed Jun. 9, 2011, under 35 U.S.C. §119(e).

TECHNICAL FIELD

This invention pertains to a unique peptide isolated from horse CC10 that can be used as a vaccine to protect horses from recurrent airway obstruction (RAO) and also to antibodies to this peptide which can be used in passive immunotherapy for short term protection against RAO or in assays to determine the level of CC10 protein in mammals. This new peptide can also be used to protect humans from asthma, based on the similarity between horse RAO and human asthma.

BACKGROUND ART

Recurrent Airway Obstruction

Recurrent Airway Obstruction (RAO), a respiratory disease similar to human asthma, is one of the most commonly diagnosed conditions affecting the lung of older horses all around world. It is a type-1 immediate hypersensitivity allergic disease involving a series of events that begin with reaginic antibodies, mainly IgE. These antibodies bind with high affinity to Fc epsilon-RI (FcεRI) receptors via the Fc portion that are found on the membrane of mast cells and basophils. Once bound, the antibodies can cross-link with environmental allergens, resulting in mast cell degranulation leading to the production of histamine and other chemical mediators that act together to induce airway inflammation. At least one reaginic antibody against *Faenia rectivirgula*, a common gram-positive bacteria, was found to be associated with lung diseases in RAO-affected and unaffected horses, finding the antibody present in about 15% in RAO-affected horses (28).

Most evidence suggests that RAO is the result of a pulmonary hypersensitivity to inhaled antigens. Exposure of affected horses to hay dust, pollens, and mold spores leads to neutrophil accumulation in the lung and bronchospasm. The identification of allergen-specific IgE in bronchoalveolar lavage (BAL) fluid and sera of affected horses supports the involvement of a late phase, IgE-mediated, hypersensitivity reaction in the pathogenesis of equine RAO. The cytokine profiles of horse affected by RAO have been measured, and a modified Th2-like immune response was thought to be involved with elevated IL-4, IL-13 and IFNg levels (6,22).

CC10 in RAO

Clara Cell 10 kDa protein (CC10) is one of the members of a family of anti-inflammatory defense proteins produced predominantly in the airway epithelium of man and animals. In humans it is also called human uteroglobin (See U.S. Pat. Nos. 6,255,281 and 7,846,899). CC10 has been shown to inhibit the entry of eosinophils and neutrophils into the human airways during inflammation in the lung, and to inhibit enzymes that release inflammatory mediators (23). Some of the members of this family have been directly linked to protection from asthma, allergy and related inflammatory responses. The gene that encodes the protein was found to be down regulated during RAO in horses (34), and the production of the CC10 protein was also reported to be reduced in RAO horses (24). The amount of CC10 in the horse serum was measured using antibodies produced in rabbits using a synthetic 21 amino acid peptide from horse CC10 (EPSKPDADMKAATTQLKTLV; SEQ ID NO:2). This peptide corresponded to amino acids 47-66 of horse CC10 protein (protein accession no. NP 001075327.1) with two amino acid variations.

A hypo-allergic vaccine to an environmental antigen of Timothy grass pollen Profilins was developed by engineering its structure (35). The engineered protein was demonstrated to induce IgG's and inhibit allergic patients' IgE antibody binding to Profilins to a similar degree as those induced by immunization with the wild type. IgG's inhibited Profilin-induced basophil degranulation. Another environmental antigen, a novel Fel d1 cat allergy vaccine, was developed that induced strong IgG response, which abrogated the allergy response in mice (32). Allergen-induced systemic basophil degranulation was shown inhibited in an Fc gamma-RIIb-dependent manner (26). In addition, antibodies have been found in healthy horses; elevated IgG response were found in healthy horses to auto antigen (1). IgGb specific to KLH was found elevated in healthy versus control horses. An inverse correlation was reported between BCG vaccination and incidence of IgE mediated allergic diseases (18). BCG immunization was demonstrated to inhibit IgE production by B cells.

Receptors for the Fc fragment of immunoglobulin-G (Fc gamma-R's) are important molecules not only to mediate and control the effectors' functions of IgG antibodies, but they also control the autoimmunity-tolerance balance in the periphery. In humans, three different types of Fc gamma-R's, belonging to the immunoglobulin gene super-family have been identified via Fc gamma-RI (CD64), Fc gamma-RII (CD32) and Fc gamma-RIII (CD16). In humans, myeloid cells express both activating and inhibitory receptors of the Fc gamma-RII family. Fc gamma-RIIA mediates processes associated with cell activation, while Fc gamma-RIIB down regulates such signaling. Differences in affinity for IgG between activating and inhibitory Fc gamma-R can result in substantial local changes in their relative concentrations with important functional consequences. Human airway smooth muscle cells express IgG-Fc gamma-RIIb with the potential to suppress remodeling and immunemodulation (36). A wide range of inflammatory and autoimmune diseases, such as vasculitis, glomerulonephritis, and autoimmune hemolytic anemia, seems to be mediated, in part, by Fc gamma-R's.

Human Asthma and Animal Models

Human asthma is a multifactorial disease, and is usually a chronic lung condition which can develop at any age and progress to a devastating disease. Asthma is classified as a hypersensitivity disease (5,30). An estimate shows that there are more than 150 million people with asthma worldwide, of which 20.3 million are in America. It is also important to note that the trend of deaths and hospitalization due to asthma is increasing in the industrialized countries of the world. Despite extensive research into the pathophysiology and treatment of asthma, high morbidity continues to threaten the human population. Because asthma can be induced by multiple stimuli, no single theory satisfactorily explains all types and cases, thus making a therapeutic regimen cumbersome.

It is a well-established fact that the salient feature of human asthma is the tendency of the affected airways to overreact to a wide variety of nonspecific stimuli, which has led to the use of bronchial provocation tests as a method to diagnose the condition (19). This hyperreactivity is characterized by hyperresponsiveness and hypersensitivity of airways to various inflammatory mediators (13). This condition can result from abnormal tissue reaction in the airways either due to intrinsic stimuli arising from a biochemical, neurological, or humoral physiological imbalance in the body or due to extrinsic stimuli arising from the environment. The changes in the environment are detected in the airway mucosa by sensory receptors, which are richly innervated by sensory (afferent) fibers. Various respirable stimuli, including charged particles, allergens, irritants, as well as heat, cold and acid, activate sensory receptors.

Animal Models of Human Asthma:

To examine various factors and mechanisms involved in pathogenesis of asthma, a number of mammalian animal models have been identified and used to study human airway hyperreactivity. For example, guinea pigs, which are not naturally susceptible to asthma, are used because of the ability to generate an experimentally-inducible model of asthma with indices similar to human asthma (14,15). Another animal model for asthma is mice which again are not naturally susceptible to asthma, but asthma can be induced experimentally. One advantage to mice is the ability to study the genetic aspects of the disease (12).

Equine Models of Human Asthma:

A major advantage to an equine model is that horses get asthma naturally like people. Horses are important for the similarity between the signs and symptoms of recurrent airway obstruction (RAO) to those of asthma, for the similarity in the nature of disease progression to human asthma, and for the ability in horses to induce or precipitate an "asthmatic" episode (7,33). Histological findings such as thickening of epithelial basement membrane, edema, inflammatory infiltrate in bronchial walls, oversized submucosal glands, hypertrophy of bronchial wall muscle, and emphysematous changes are observed in both human asthma and in equine RAO (6,7,33). One difference is that the cellular infiltrate in RAO is mostly neutrophils, whereas esosinophils are more common with human asthma. Recently, identification of persistent nuclear factor kappa-B (NF-$_K$B) activity in asthma and RAO clearly suggests that equine RAO is a better animal model of human asthma than those of other mammalian species (8,20). Chronic obstructive pulmonary disease (COPD) in horses, commonly called heaves, and currently termed recurrent airway obstruction (RAO), is an airway hyperreactivity disease comparable to human asthma (7,33). Horses with heaves spontaneously develop acute bronchiolitis after exposure to antigens such as hay or pasture mold. Heaves is a more common condition in temperate climatic regions where horses are confined in stables during winter seasons and where they are house near stored hay. Another form of RAO seen in the southern regions of the U.S. is summer pasture-associated obstructive pulmonary disease (SPAOPD), caused by allowing horses to graze on lush pasture in the humid summer months where molds and pollens in the grass serve as antigen stimulation (4). Both forms of RAO share common signs and symptoms (4,6,11). The clinically abnormal condition of RAO is characterized by hyperreactivity of airways to antigens, inflammatory mediators and various other external stimuli. The condition also presents a decreased dynamic compliance of lung and increased airflow resistance to histamine- or methacholine-challenges, which are the common tests performed for diagnosing either human asthma or equine RAO. When horses are exposed to diverse stimuli such as allergens or respirable irritants in the environment, their airways react with a specific response that includes infiltration of inflammatory cells in the lungs, damage of airway epithelium, and inflammatory mediator release. This reaction primes the airways to respond excessively to a broader range of stimuli. Continued stimulation leads to airway hyperreactivity, which is characterized by hypersensitivity (increased sensitivity of airway smooth muscles) and hyperresponsiveness (increased magnitude of smooth muscle contractility) to diverse stimuli as observed in human asthma (3,6,7,11). Thus, RAO in horses shares several common features of human asthma, such as airway hyperreactivity, severe bronchoconstriction, increased mucus production, presence of airway inflammatory mediators in bronchoalveolar lavage fluids, infiltration of inflammatory cells, difficulty in breathing and exercise intolerance. Horses then have several advantages as an animal model for human asthma. Of course, the main disadvantages to using horses are size and cost to obtain and house.

U.S. Pat. Nos. 7,846,899 and 6,255,281 and U.S. Patent Application Publication No. 2005/0261180 describe the use of recombinant human CC10 (also referred to as human uteroglobin) and its use in various human inflammatory and respiratory disorders.

U.S. Patent Application Publication No. 2011/0240012 describes the use of recombinant human CC10 and methods to administer CC10 nasally, and its use in treatment of various nasal inflammatory diseases, including rhinitis and sinusitis.

DISCLOSURE OF INVENTION

We have discovered a 21 amino acid (aa) peptide (Peptide-1; SEQ ID NO: 1; KNTKDSILKLMDKIAKSPLCA) based on the C-terminal of Equine CC10 that can be used as a vaccine to protect horses from RAO, and protect humans from asthma. We have produced a rabbit polyclonal antibody to this peptide, and validated the specificity of antibody by ELISA. We tested the sera of healthy and RAO affected horses for CC10 using this antibody in a competitive inhibition ELISA, and surprisingly found that sera from some of the healthy horses showed significantly higher titers than the maximum titer expected with the control. This result could only be explained if horse sera itself had antibodies to Peptide-1, suggesting that healthy horses are protected from RAO by antibodies similar to the polyclonal antibodies produced by Peptide-1. We believe that such auto-antibodies may be the result of exposure to environmental allergens that have 'molecular mimicry' to the sequence of Peptide-1. To confirm this belief, we performed a sequence analysis using the BLAST algorithm and found that several known natural antigens have a similar sequence to Peptide-1. We have identified a unique isolated peptide sequence (Peptide-1) which can be used as a vaccine for protection of horses from RAO and seasonal allergy. The advantages to Peptide-1 are: (1) it may be used in young animals as a vaccine to protect them from RAO later in life; (2) antibodies to Peptide-1 may be administered for short-term passive immunotherapy to RAO-affected horses; and (3) antibodies to Peptide-1 can be used in measuring the level of CC10 protein in animals to identify potential RAO horses (horses with reduced CC10). In addition due to the homology with the human protein CC10 and since human seasonal allergy (or asthma) has the same mechanism of induction as horse RAO, we believe that this Peptide-1 or homologous sequences or its antibodies may be useful therapeutically in humans for protection against or alleviating the symptoms of asthma.

MODES FOR CARRYING OUT THE INVENTION

Figure 1:
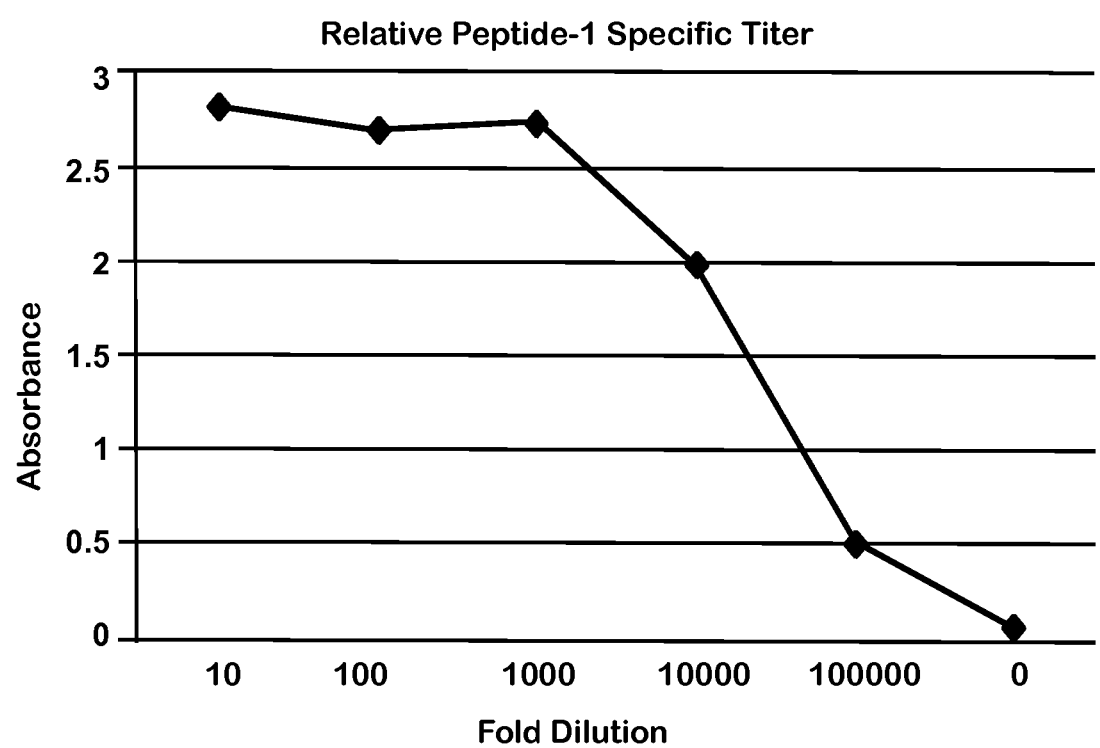
FIG. 1 illustrates the results of an antibody capture endpoint ELISA showing the Peptide-1 specific antibody titer with Peptide-1 as the capture antigen, peroxidase-conjugated goat anti-rabbit IgG as the detection antibody, and the isolated rabbit antibody at several dilutions.

The term "Peptide-1" refers to a 21 amino acid (aa) peptide (Peptide-1; SEQ ID NO: 1; KNTKDSILKLMDKI-AKSPLCA) based on the C-terminal of Equine CC10 that can be used as a vaccine to protect mammals from a respiratory airway disorder. This invention relates not only to a functional Peptide-1 as described in this specification, but also to peptides having modifications to such a sequence resulting in an amino acid sequence having the same function (i.e., the ability to be used as a vaccine for protection against antigen-caused respiratory disorders), and about 80%, preferably 85%, and more preferably 90% homology to the sequence of the amino acid sequence as described, and most preferably about 95% or greater homology, particularly in conserved regions. "Homology" as used here means identical amino acids or conservative substitutions (e.g., acidic for acidic, basic for basic, polar for polar, nonpolar for nonpolar, aromatic for aromatic). The degree of homology can be determined by simple alignment based on programs known in the art, such as, for example, GAP and PILEUP by GCG, or the BLAST software available through the NIH internet site. Most preferably, a certain percentage of "homology" would be that percentage of identical amino acids.

The term "vaccine" refers to a composition or compound (an antigen) used to stimulate an immune response in a mammal and so confer resistance to the disease or infection in that mammal, including an ability of the immune system to remember the previously encountered antigen. Antibodies are produced as a result of the first exposure to an antigen and stored in the event of subsequent exposure.

The term "adjuvant" refers to non-antigenic substance that, in combination with an antigen, enhances antibody production by inducing an inflammatory or other non-defined response, which leads to a local influx of antibody-forming cells. Adjuvants are used therapeutically in the preparation of vaccines, since they increase the production of antibodies against small quantities of antigen, lengthen the period of antibody production, and tend to induce memory cell responses. Such adjuvants could include, but are not limited to, complete Freund's adjuvant, incomplete Freund's adjuvant, aluminium hydroxide, dimethyldiocta-decylammonium bromide, Adjuvax (Alpha-Beta Technology), Imject Alum (Pierce), Monophosphoryl Lipid A (Ribi Immunochem Research), MPL+TDM (Ribi Immunochem Research), Titermax (CytRx), toxins, toxoids, glycoproteins, lipids, glycolipids, bacterial cell walls, subunits (bacterial or viral), carbohydrate moieties (mono-, di-, tri- tetra-, oligo- and polysaccharide) various liposome formulations or saponins Alum is the adjuvant currently in use for human patients. However, for horses, incomplete Freund's adjuvant may be used.

The term "immune response" refers to the reaction of the body to an antigen, which is usually a foreign or potentially dangerous substances (antigens), particularly disease-producing microorganisms. However, in the current technology, a new peptide sequence that is similar to an endogenously produced defense protein (CC10) is used for the antigen. The response involves the production by specialized white blood cells (lymphocytes) of proteins known as antibodies, which react with the antigens to render them harmless. The antibody-antigen reaction is highly specific. Vaccines also stimulate immune responses.

The term "immunologically effective amount" refers to the quantity of an immune response inducing substance required to induce the necessary immunological memory required for an effective vaccine. For example, Peptide-1 at a dose of 0.1 mg/kg body weight when given subcutaneously has been found an immunologically effective amount.

The pharmaceutical compositions of the present invention are advantageously administered in the form of injectable compositions. A typical composition for such purpose comprises a pharmaceutically acceptable carrier. For instance, the composition may contain human serum albumin in a phosphate buffer containing NaCl. Other pharmaceutically acceptable carriers include aqueous solutions, non-toxic excipients, including salts, preservatives, buffers and the like (REMINGTON'S PHARMACEUTICAL SCIENCES, 15th Ed., Easton ed., Mack Publishing Co., pp 1405-1412 and 1461-1487 (1975) and THE NATIONAL FORMULARY XIV, 14th Ed., American Pharmaceutical Association, Wash., D.C. (1975), both hereby incorporated by reference). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. The pH and exact concentration of the various components the pharmaceutical composition are adjusted according to routine skills in the art. Goodman and Gilman, THE PHARMACOLOGICAL BASIS FOR THERAPEUTICS (7th ed.).

In addition for a small peptide, the peptide may be covalently linked to an immunogenic protein carrier to increase its recognition by the immune system as foreign. Common protein carriers include keyhole limpet hemocyanin (KLH). Bovine serum albumin (BSA), chicken egg albumin (OVA), and immunoglublin Fc fragment. Recently, non-proteinic nanoparticles have been used as carriers.

Typically, such vaccines are prepared as injectables, either as liquid solutions or suspensions; solid forms suitable for solution in, or suspension in, liquid prior to injection may also be prepared. The preparation also may be emulsified. The active immunogenic ingredient is often mixed with an excipient that is pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH-buffering agents, adjuvants or immunopotentiators that enhance the effectiveness of the vaccine.

The vaccines are conventionally administered intraperitoneally, intramuscularly, intradermally, subcutaneously, orally, nasally, or parenterally. Additional formulations are suitable for other modes of administration and include oral formulations. Oral formulations include such typical excipients as, for example, pharmaceutical grades of mannitol, lactose, starch, magnesium stearate, sodium saccharine, cellulose, magnesium carbonate and the like. Additionally, the peptide can be encapsulated in a sustained release formulations or a coating that resist the acidic pH of the stomach. The compositions take the form of solutions, suspensions, tablets, pills, capsules, sustained release formulations or powders and contain 10%-95% of active ingredient, preferably 25-70%. In a preferred solution, equal volumes of Peptide-1 conjugated with KLH and Incomplete Freund's adjuvant were used in a subcutaneous injection. Other possible routes of administration is to use a DNA expression vector with a nucleic acid sequence encoding the Peptide 1 (SEQ ID NO:1) for immunization using intradermal or intramuscular techniques.

The dose to be administered depends on a predetermined quantity of active material calculated to produce the desired therapeutic effect in association with the required diluent, i.e., carrier or vehicle, and a particular treatment regimen. The quantity to be administered, both according to number of treatments and amount, depends on the subject to be treated, capacity of the subject's immune system to synthesize antibodies, and degree of protection desired. The precise amounts of active ingredient required to be administered depend on the judgment of the practitioner and are peculiar to each individual. However, suitable dosage ranges are on the order of one to several hundred micrograms of active ingredient per individual subject. Suitable regimes for initial administration and booster shots also vary but are typified by an initial administration followed in one or two week intervals by one or more subsequent injections or other administration Annual boosters may be used for continued protection.

Example 1

Development of CC10 Peptide Antibody

An isolated 21-amino acid peptide was designed and made based on the 'C' terminal 21 amino acid peptide of Equine CC10 protein (Accession no. NP_001075327.1) ("Peptide-1; SEQ ID NO:1; KNTKDSILKLMDKIAK-SPLCA). The sequence of this peptide corresponds to amino acids 71-91 of equine CC10 and does not overlap with that of the peptide (amino acids 47-66) previously used to make rabbit antibodies (24). Peptide-1 was used to develop rabbit polyclonal antibodies. Briefly, Peptide-1 was conjugated to the carrier protein KLH (Keyhole Limpet Hemocyanin), and the conjugate used to immunize naïve rabbits to induce an immune response. Antibodies were purified from serum of immunized rabbits by established chromatographic techniques as described previously (21). The rabbit antibody was verified in an antibody capture endpoint Enzyme-Linked ImmunoSorbent Assay (ELISA) with Peptide-1 as the capture antigen and peroxidase conjugated goat anti-rabbit IgG (Jackson ImmunoResearch Laboratories, Inc., West Grove, Pa.) as the detection antibody as described previously (9). As shown in FIG. 1, the rabbit antibody had a titer of >100,000 with an optimum detection range between 1000 and 10,000 dilutions (FIG. 1).

Example 2

Development of a Competitive Inhibition ELISA Assay

Figure 2:
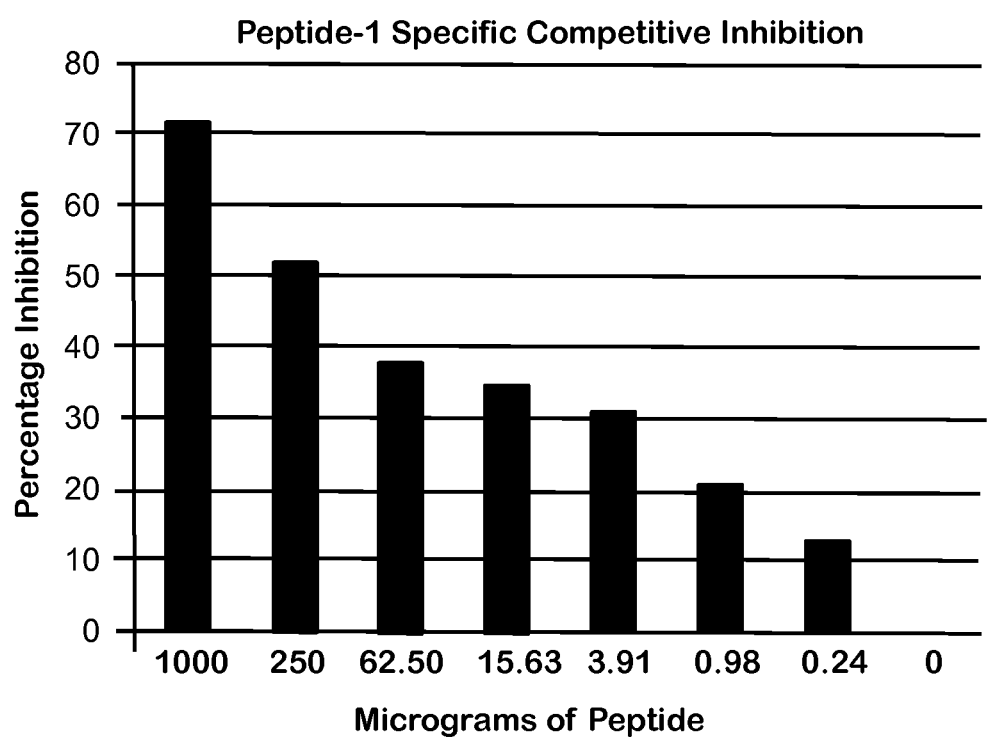
FIG. 2 illustrates the results of a competitive inhibition ELISA assay using a series of concentrations of Peptide-1.

Based on the results in FIG. 1, a 1:5000 dilution of this antibody was used for further CC10 detection in a competitive ELISA. To validate the competitive inhibition assay, a series of Peptide-1 dilutions starting at 1000 µg/mL was prepared. From each dilution, 50 µL was mixed with 50 µL of a solution of 1:5000 diluted rabbit polyclonal antibody. This mixture was incubated for 30 min, and then used in ELISA with a Peptide-1 coated plate as described previously (9). As shown in FIG. 2, the inhibition of antibody binding to peptide coated plated was dependent on Peptide-1 concentration.

Example 3

Determination of CC10 Specific IgG Titer—Elevated CC10 IgG Titer

Figure 3:
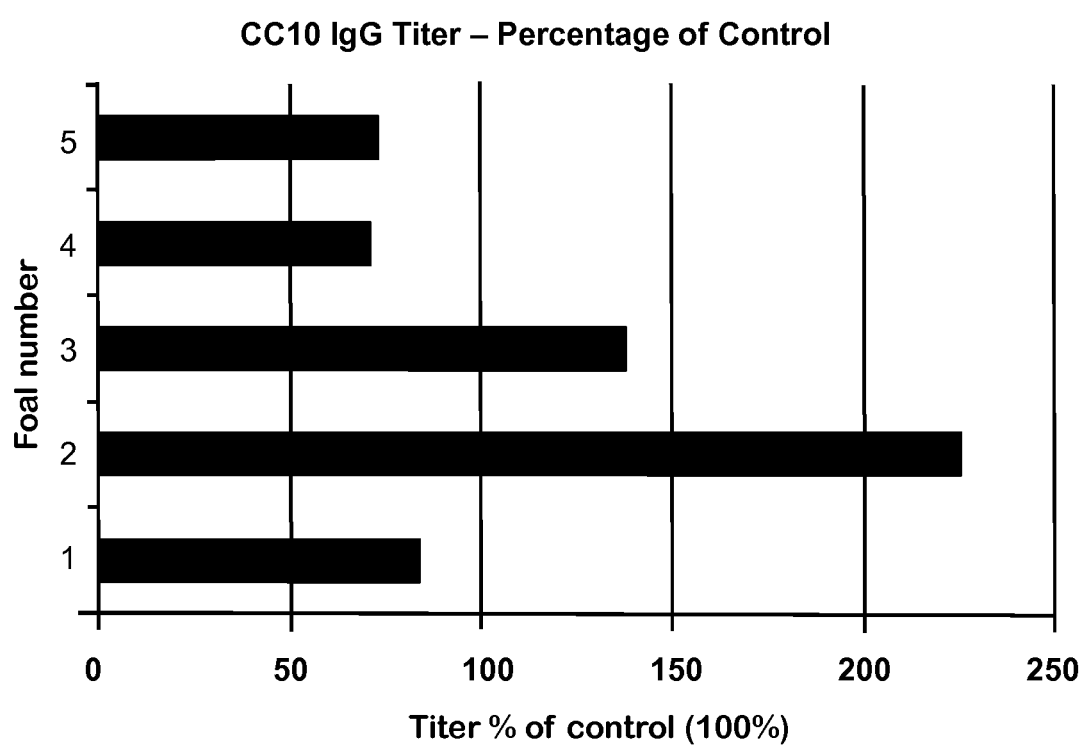
FIG. 3 illustrates the amount of CC10 IgG titer from five healthy horses (without RAO) as compared to the control as measured using competitive inhibition ELISA assay.

The competitive ELISA system as described above (Example 2) was used to measure relative levels of CC10 in the serum of 5 healthy and 5 RAO horses. Briefly, 10 µL of serum from each horse was mixed with 50 µL of a 1:5000 diluted rabbit antibody to Peptide-1 and incubated at 37° C. for 30 min. This serum-antibody mixture was then added to wells on ELISA plate pre-coated with Peptide-1 and blocked with 2% milk powder proteins (Carnation Milk, Nestle). The amount of free peptide specific rabbit antibody available to bind to Peptide-1 coated on the plate varied, depending on the amount of native CC10 present in the serum sample. Plates were washed, and the amount of rabbit IgG bound to the plate was measured using Goat anti-rabbit IgG-HRP (Jackson ImmunoResearch Laboratories, Inc.). Surprisingly, some of the healthy horses had a significantly high titer than the control samples which had only rabbit peptide IgG without the addition of any horse sera. In FIG. 3, the absorbance titer data for healthy horses was normalized to that of control as 100%. Two of the five healthy horses, or 40%, showed significantly increased titer for CC10 in sera over that of the controls.

The titer levels were too significant to consider the levels as resulting from non-specific binding of IgG present in horse serum. Without wishing to be bound by this theory, we believe that at least some healthy horses have significant IgG antibody levels already that would bind to the 21 amino acid peptide (Peptide-1) of CC10. The goat anti-IgG to rabbit was used for detection, and it is a pan specific antibody that is cross-reactive across many species including horse IgG. Such auto-antibodies in the horse serum may be produced due to exposure to environmental allergens that show 'molecular mimicry' to the sequence of Peptide-1. As described below, a sequence analysis using the BLAST algorithm as previously described (9) was conducted, and found that several known antigens in nature have a similar sequence to Peptide-1.

Example 4

BLAST Sequence Homology Analysis—Homology to Microbial Antigens, Molecular Mimicry The Peptide-1 sequence was used in a protein BLAST sequence analysis against published bacterial and fungal proteins. High homology to some bacterial and fungal proteins including to *Aspergillus*, a known environmental allergen was found. (Table 1).

TABLE 1

| No. | Protein ID | Species | % Identity |
|---|---|---|---|
| 1. | Q65R19_MANSM AspA Protein | *Mannheimia succiniciproducens* (Bovine rumen bacteria) | 90% |
| 2. | D3V5R2_XENBV | *Xenorhabdus bovienii* (bacteria found in nematodes) | 71% |
| 3. | C4VBG4_NOSCE | *Nosema ceranae* (microsporidium usually affecting bees) | 58% |
| 4. | A2R1F5_ASPNC | *Aspergillus niger* (common soil and plant fungus) | 61% |

BLAST searches using the whole horse CC10 was also conducted and found significant homology to a cat allergen Fel d1 and to a putative U1p1 protease protein in *Aspergillus fumigatus* (Table 2).

TABLE 2

| No. | Protein ID | Species | % Identity |
|---|---|---|---|
| 1. | P30438.2 Fel d1 | *Felis catus* (domestic cat) | 37% |
| 2. | NC_007198.1 U1p1 protease | *Aspergillus fumigatus* (fungus commonly found in soil) | 51% |

Example 5

Elevated Peptide-1 Specific IgG in Healthy Horses

Figure 4:
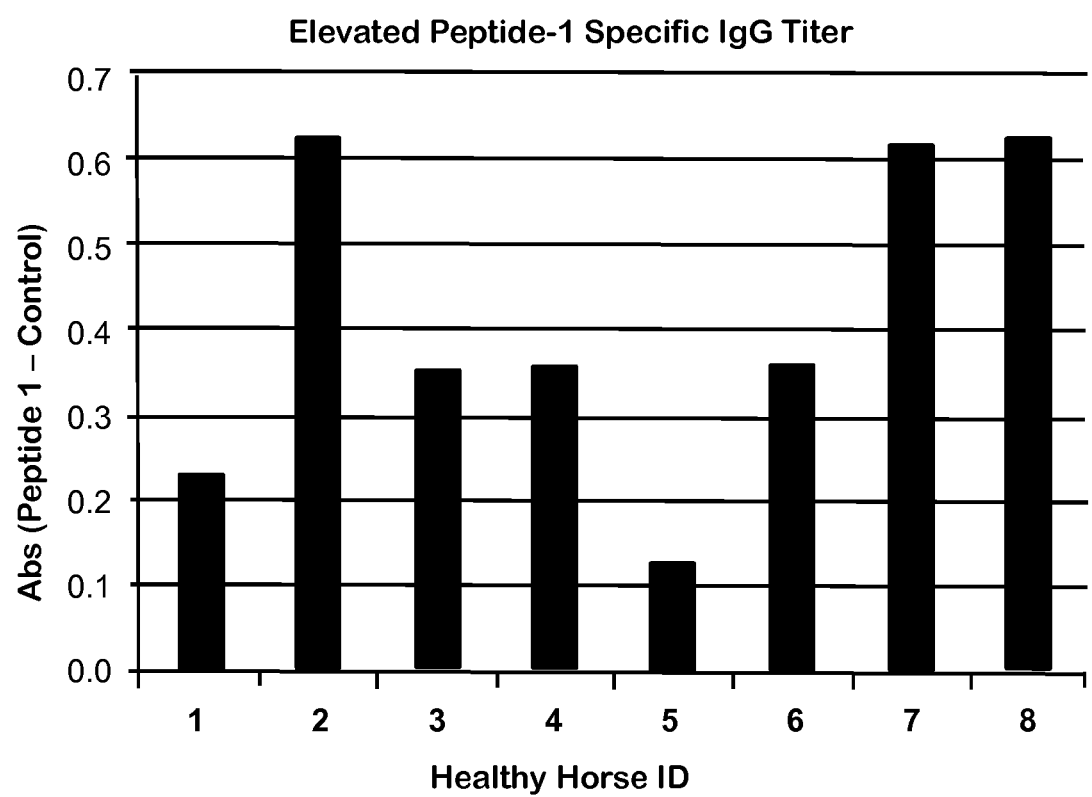
FIG. 4 illustrates the amount of Peptide-1 specific IgG titer using a direct sandwich ELISA and measuring serum from eight healthy horses standardizing the value by subtracting the control value of UGRP peptide from the experimental values for CC10.

To further validate if an elevated CC10 specific IgG antibody titer existed in healthy horses, sera from eight healthy horses with no sign of RAO were collected. To determine levels of Peptide-1 specific IgG titer, a direct sandwich ELISA was used according to published protocols (18). Diluted healthy horse serum samples were added to a plate coated with Peptide-1. The peptide bound horse IgG antibody was then detected using peroxidase conjugated goat anti horse IgG antibody (Jackson ImmunoResearch Laboratories, Inc.). As control, a 17 amino acid 'C' terminal peptide from UGRP1 protein (another member of the CC10 family) was used. As shown in FIG. 4, elevated amounts of antibodies to Peptide-1 was again found in healthy horses. This result further supported that Peptide-1 specific IgG is present in many healthy horses (FIG. 4).

These results confirm that elevated levels of Peptide-1 specific antibodies are found in healthy horses. Without wishing to be bound by this theory, we believe that this elevated level is due to molecular mimicry. Homology of a self-protein to a microbial protein can induce antibody response to the self-antigen if exposed to the microbial or fungal product early in life. Sequence analysis as shown above indicated a high homology of Peptide-1 to some microbial and fungal proteins including *Aspergillus*, a known environmental allergen. It is possible that augmented immune responses generated in these healthy horses early in life afforded them protection subsequently in life.

The hygiene hypothesis suggests that a reduced frequency of infections, less severe infection, and prevention of infection (for example, by a frequent use of antibiotics) would prevent maturation of Th-1 immunity and, therefore, would give rise to an allergen-specific Th-2 immune response following natural exposure to allergens. The immunological explanation for the "hygiene hypothesis" has been proposed to be the induction of T helper 1 (Th1) responses by microbial products. However, the protective results of hygiene hypothesis-linked microbial exposures are currently shown to be unlikely to result from a Th1-skewed response. The hygiene hypothesis has been proposed to be more important in regulating the PMN-dominant inflammatory response than in inducing a Th1-dominant response (10). Endotoxins, part of the outer membrane of Gram negative bacteria, are a potent inducer of neutrophilic airway inflammation. The risk of non-atopic asthma, characterized by neutrophilic response, is enhanced in subjects with higher endotoxin exposure. This information is in accordance with the so-called hygiene hypothesis and have been supported by animal studies and at the cellular level (11). Thus vaccinating the horses at a young age with Peptide-1 will produce protective immune response which will protect them from environmental allergens.

Auto-antibodies to equine CC10 'C' terminal 21 amino acid peptide (Peptide-1) were observed in horses resistant to RAO. Sequence analysis showed some homology of Peptide-1 to several bacterial and fungal sequences. Therefore, it is possible that the antibodies were developed due to molecular mimicry to microbial antigens. Activation of B-cells carrying Fc gamma-RII receptor by these autoantibodies may be protective, while activation of Fc∊R1 receptor induces disease. Immunization of horses with Peptide-1 early in life can provide protection from RAO later in life.

Peptide-1 can be used as a vaccine for young horses to protect them from developing the respiratory allergy later in their life. In addition, the antibody produced to Peptide-1 can be used in passive immunotherapy for short term therapy to decrease the symptoms of a horse or other mammal with respiratory airway disease. Antibodies to Peptide-1 can also be used to determine the level of CC10 protein in horses. A decreased level of CC10 in the serum could be a biomarker for detecting horses that are vulnerable to RAO which will facilitate early selection and improved breeding. In addition, Peptide-1 or similar peptide may also be useful in developing a vaccine to protect people that are susceptible to allergic diseases such as human asthma.

Example 6

Vaccination of Foals with Peptide-1

A pilot study in foals was started in January 2012 to determine whether an immune response could be generated by vaccinating foals with Peptide-1, a newly identified peptide from Clara Cell proteins of horses. The study was approved by the Institutional Animal Care and Use Committee (IACUC) of Louisiana State University to be conducted in nine Shetland foals. The foals were obtained from the Equine Health Studies Program of the LSU School of Veterinary Medicine, Baton Rouge, La. 70803. They ranged in age from 4 to about 6 months. This study is still continuing. So far Peptide-1 has been injected into 3 foals, but all nine foals will be injected in a manner similar to that described below. The body weights of the three foals injected ranged from about 101 to about 112 kg.

The foals were selected based on a thorough physical examination by a board certified equine clinician and a complete blood count (CBC) was performed to determine any clinical pathology. Since Peptide-1 is a small peptide, it was covalently conjugated with a large carrier protein, Keyhole Limpet Hemocyanin (KLH), for easy recognition by the lymphocytes to produce antibody production. KLH is a commonly used as a carrier protein.

Two days before the injection of the peptide-1, a foal along with the mare was brought from the pasture to a bedded stall of the LSU School of Veterinary Medicine. They were fed hay and concentrated horse chow (Horse Chow #200$^R$, Purina Mills, St. Louis, Mo.); water was provided ad libitum. A physical examination was conducted on the day of injection. The foal's body temperature, heart rate, respiratory rate, body weight, body score, sex, breed, age and general physical conditions were recorded. After the physical examination, 5 ml of blood was drawn from jugular vein to determine pre-immune antibody titer (control value) and CBC.

Foal #1:

Since the peptide-1 has not been tried in any animals, the first foal was used to test the injection method and dosage. A low dose of 0.1 mg/kg body weight of conjugated peptide-1 with KLH was used, but without an adjuvant to minimize any adverse reactions due to either a high dose of peptide-1 or adjuvant. This protocol allowed a determination of any reaction due to the conjugated peptide-1 alone. A subcutaneous route of administration was chosen to produce a consistent "slow and steady" absorption. The first injection was given on the left side of the neck after cleaning with alcohol. No major adverse reaction was observed at the site of injection or on the animal as a whole. A small swelling was observed at the site of injection which disappeared after two days. The foal did not have any fever or any other clinical pathological changes. After the injection, 5 ml blood was collected weekly. A booster injection with the same dose and route was given on the right side of the neck on the 15$^{th}$ day following the initial injection. Weekly blood collections continued for 42 days. The antibody titer did not change from the pre-immune values in this foal (Data not shown). For the remaining foals, a new protocol was used in that an adjuvant was added to the injection and the booster injection was given on the 28$^{th}$ day after the initial injection.

Foal #2

The same protocol as described above for Foal #1 was used in this foal except for the addition of the adjuvant and a change in booster injection time. An equal volume of Incomplete Freund's Adjuvant (IFA; Sigma Chemicals, St. Louis, Mo.) and Peptide-1 was mixed well and administered subcutaneously. The total volume of injection did not exceed 2 ml, and the does of Peptide-1 remained as in Foal #1. Prior to the first injection and weekly thereafter, 5 ml blood was drawn for analysis. A booster injection of adjuvant/Peptide-1 was given on the 28$^{th}$ day following the initial injection.

Immediately after injection (either the first injection or the booster), a small swelling (size 1"×0.5") at the site of injection was observed. The foal was observed continuously for the first hour and later every hour for eight hours. The foal evinced pain upon touch at the injection site, but it was eating, nursing, and drinking within 15 minutes after injection. The foal showed no other adverse reaction, and it was bright, alert and responsive. No sweating, fever, cough, seizure or difficulty in breathing was observed.

By the end of 24 h, the swelling at the injection site had spread to an area of 2.5"×2" size, and had a thickness of only 0.5". The foal remained under close observation for another two days, when the swelling began to subside. On the third day, foal and mare were allowed to go to the pasture. A similar swelling occurred at the booster injection time also. Therefore, in the animal protocol, foals would be kept in the bedded stall with the mare for a week after injection to observe the foals closely. In addition, the protocol demanded that if the swollen area is more than 2.5" in diameter and more than 0.5" in thickness, hot water packs are to be applied to relieve pain and swelling. Veterinary medical care is to be consulted if the condition worsens. After one week in the stall, the Foal #2 was let out to pasture and continued to do well for the remainder of the experimental period of 57 days.

Figure 5A:
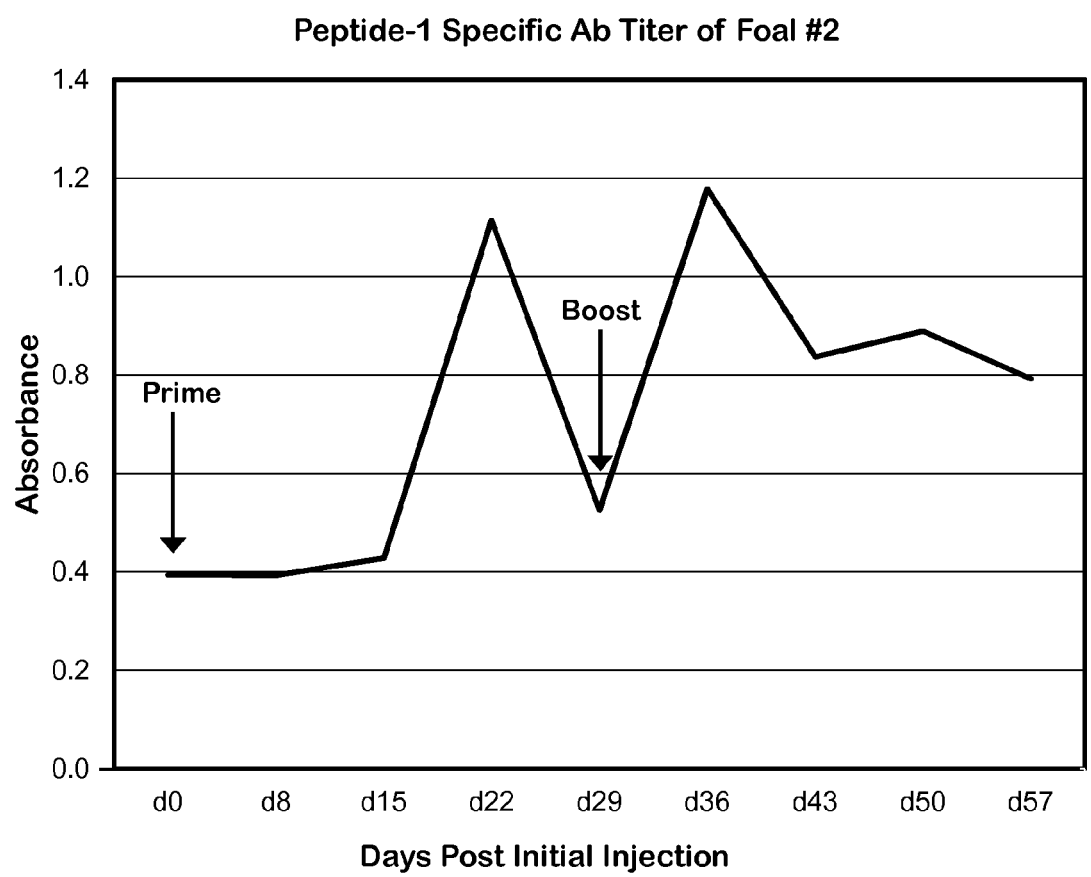
FIG. 5A illustrates the amount of Peptide-1 specific IgG titer in serum from Foal #2 primed on day 0 and boosted on day 29 by subcutaneous injection of 0.1 mg/kg Peptide-1. Antibody titer determined using a direct sandwich end point ELISA with Peptide-1 as a capture antigen and peroxidase conjugated goat anti-equine IgG as a detection antibody.

The peptide-1 specific total IgG antibody titers were determined in the serum samples by enzyme labeled immune sorbent assay (ELISA). So far, eight samples have been tested in this foal for a time period of 57 days. The results are shown in FIG. 5A. The samples were taken on pre-injection serum collected on day 0, and then every seven days thereafter. The results indicate that the antibody titer to Peptide-1 increased exponentially after day 15 up to day 22, when there was a drop. After the booster on day 29, the antibody titer increased to a peak level at day 36, but remained at elevated levels for the remaining period. As shown in FIG. 5A, Peptide-1 at a dose of 0.1 mg/kg when injected subcutaneously with an adjuvant can produce significant amounts of antibodies. We believe that this increase in antibodies to Peptide-1 will immunize these young horses and protect them from recurrent airway obstruction (RAO). We also believe that the purified antibodies produced in the foal can be isolated and given to adult horses to protect horses with a history of RAO (susceptible horses).

Foal #3

The basic protocol is as described for Foal #2. However, before injecting the peptide, extra care was taken in cleaning the injection site by scrubbing the site with Septisol antiseptic foam (Septisol$^R$, Steris Corp., Ohio) and alcohol. This additional step reduced the swelling considerably over what was seen in Foal #2. There was a small swelling in this foal which lasted only for 24 hours, probably due to the adjuvant. The adjuvant has an oily consistency, which would facilitate slow absorption of the injected solution.

Figure 5B:
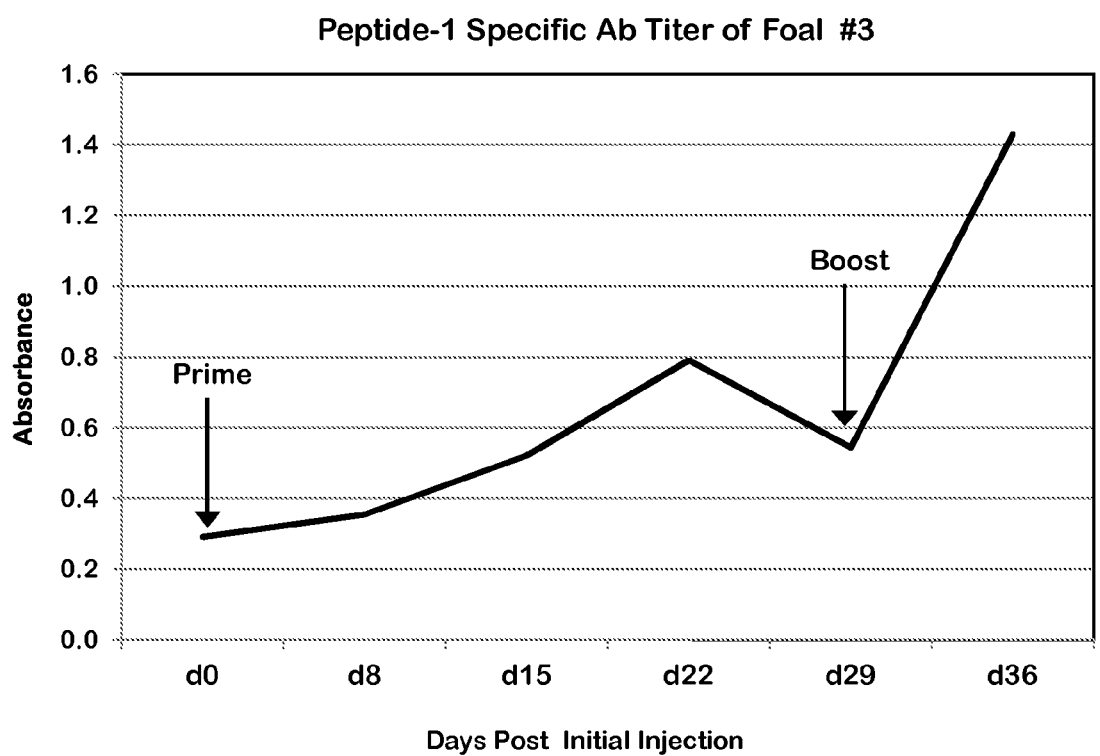
FIG. 5B illustrates the amount of Peptide-1 specific IgG titer in serum from Foal #3 primed on day 0 and boosted on day 29 by subcutaneous injection of 0.1 mg/kg Peptide-1. Antibody titer determined using a direct sandwich end point ELISA with Peptide-1 as a capture antigen and peroxidase conjugated goat anti-equine IgG as a detection antibody.

Foal #3 is still being followed. The results to date are shown in FIG. 5B. As shown in FIG. 5B, the antibody titer did not increase until about day 15, similar to Foal #2. It then peaked on day 22, and then again after the booster on day 29. The response curve for this foal closely follows the response curve of Foal #2, confirming the effectiveness of Peptide-1 in producing antibodies.

Future Studies in Foals

Thus far, only a single dose and route have been tried. In future studies with foals, a lower (0.03 mg/kg) and a higher dose (0.3 mg/kg) of the peptide-1 will be tried to show what difference in response can be expected with one log dose difference. Administration of a higher dose and observation of the foal for adverse reactions will also demonstrate if any toxicity exists with the peptide. With large animals such as horses, determination of $LD_{50}$ (lethal dose for 50% of the animals tested) is not usually performed. In addition, a nasal route of administering Peptide-1 will be tried because of its convenience to use.

Example 7

Use of Peptide-1 or its Antibodies to Protect Adult Horses

Peptide-1 will be used to vaccinate adult horses, or antibodies to Peptide-1 will be used for short term protection for adult horses. Initial experiments will determine the effectiveness of use of the peptide or its antibody to protect adult horses from recurrent airway obstruction (RAO). Experiments to achieve the following three objectives will be conducted: (1) a determination of the antibody levels in horses that receive two subcutaneous injections of the peptide one month apart; (2) a determination of whether the horses can maintain a sufficient titer of antibody for immunity from an injection given during the remission period; and (3) a determination of whether horses that receive the peptide injection or an injection of antibodies are resistant to RAO or develop lesser symptoms of RAO.

Following approval from the IACUC, this study will be performed in 6 horses that are known to be susceptible to RAO (3 for injection of Peptide-1 (the "active immunity" group), and 3 for injection of antibodies (the "immunotherapy" group)). Horses with a history of RAO will be obtained by donation to the LSU School of Veterinary Medicine. Susceptibility to RAO in the horses will be determined on the basis of their history of the disease, physical examination, clinical scoring based on signs of RAO, pulmonary function testing (determining transpleural pressure (Ppl)), and bronchoalveolar (BAL) fluid examination. None of the horses will have received medications within 10 days prior to the assessment. Three horses will be injected with the peptide, and 3 will be injected with antibody to Peptide-1. The antibodies will be extracted from the blood of foals that were injected with Peptide-1 as described above. A onetime collection of blood of 450 ml from each foal will be collected. If adult horses, as expected, maintain high antibody titer values after injection of Peptide-1, antibody from the adult horses can also be used. The sera with high antibody titers value will be pooled for purification and antibody extraction.

Techniques for Selection of Horses, Antibody Titer Determination & Antibody Extraction.

Transpleural pressure determination: The change in transpleural pressure (Ppl) will be measured indirectly as previously described (31,34). Briefly, a 10-cm long 3.5-cm circumference esophageal balloon will be secured at one end of a catheter (PE tubing 350). The catheter will be connected to a pressure transducer (model PESO) interfaced with a polygraph (Grass model 7D). The balloon will be inserted through a lubricated nasogastric tube (bigger tube) placed in the rostral esophagus. Once the balloon is located between the heart and the diaphragm, the nasogastric tube will be removed. The balloon will be inflated with 1.5 ml of water, and 10 measurements will be recorded. Changes in esophageal pressure (peak inspiratory pressure minus peak expiratory pressure) during tidal breathing will reflect the change in Ppl (measures as cm $H_2O$). Horses with a Ppl of about 15 or greater will be selected for the study. This measurement will help confirm the horse has RAO and will get episodes of the disease seasonally.

Bronchoalveolar Lavage (BAL) Fluid Collection:

Horses will be sedated using a combination of xylazine hydrochloride (0.5 mg/kg, given intravenously (IV)) and butorphanol tartarate (11 mg/kg, IV). After placement of a nose twitch, a 244-cm (11-mm outer diameter, 3-mm inner diameter) flexible silicone tube will be passed through the nasal passage into the trachea to wedge in the distal airway. As the silicone tube is advanced through the trachea and carina, 30 mL of 1% lidocaine will be injected through the tube and followed by 30 mL of air. The cuff will be inflated with 4 mL of air, and five 60-mL aliquots of sterile 0.9% saline will be infused manually with 60 mL syringes. Immediately after infusion, bronchoalveolar lavage fluid (BALF) will be collected and pooled into a sterile flask. Cytological analysis of BAL fluid will demonstrate whether the horses have any other respiratory problem (10,31)

Clinical Scoring:

The horses will be assigned a clinical score (CS). The CS is determined by the following algorithm (31, 34.

$$CS = \frac{\text{(Medial nostril flare + lateral nostril flare)}}{2} + \text{Abdominal lift}$$

Each of these variables in the formula is scored from 0 to 4. The zero score indicates the nostril has little movement, and the ventral flank shows little or no movement. A score of 4 indicates the nostril remains maximally flared throughout the respiratory cycle and abdominal lift resulting in a "heave line" extending cranially to the $5^{th}$ intercostal space. Thus, the maximum CS is 8. Clinically healthy horses will have clinical scores <4.0. RAO horses will have a score of >5.0. This non-invasive procedure will show whether the animal has RAO.

Blood Collection:

Foals that have previously injected with Peptide-1 will be used to supply antibodies to Peptide-1 as discussed above. A one-time sample of 450 ml blood will be collected from each foal, all of whom are currently above 200 lb body weight. For adult horses, 10 ml blood will be collected from the adult horses before the injection (peptide or antibody) and weekly thereafter until the season (June, July, August) is over.

Antibody Extraction:

Total IgG antibody from hyper-immune sera collected from foals will be purified by Protein-A/G affinity chromatography, by established procedures (2). Briefly, IgG from sera will be allowed to bind to Protein-A/G conjugated agarose beads in a chromatography column. After washing off all unbound serum proteins, Protein-A/G bound IgG will be eluted out by lowering pH to 2.5. Antibodies will stored in –80° C.

Antibody Titer Determination by ELISA: Relative Antibody Titer Will be Determined by sandwich ELISA by a well-established protocol (17), and as described above. Briefly, ELISA plate will be coated with Peptide-1. Serial 10 fold dilutions of sera up to 100,000 will be used as a sample. After washing all unbound proteins from the plate, the amount of bound IgG specific to Peptide-1, will be determined by a secondary antibody, peroxidase-conjugated goat anti-horse IgG (17).

Experimental Protocol:

Eight adult horses that have a history of RAO will be clinically scored and pulmonary function tested during the active RAO period (June, July, August & may be September). This will confirm their susceptibility to RAO. The horses will remain in the pasture for the complete RAO season. After the RAO season, the horses will begin to undergo remission, and by November, will not show active signs of RAO. Without treatment, the RAO will return in the next RAO season, starting in June. This initial season of monitoring will allow each horse to be used as its own control.

One month before the beginning of the second RAO season, 3 horses will be given antibodies at a dose of 1 mg/kg body weight subcutaneously. A day before the injection, a horse will be brought to a bedded stall. The horse will be fed hay and concentrates; and water will be given ad libitum. A 10-ml blood sample will be drawn for determining CBC and antibody titer. A thorough physical examination including body temperature, heart rate, respiratory rate, body weight, body score, sex, breed age and general physical conditions will be recorded.

The following day, purified antibody at a dose of 1 mg/kg body weight will be administered subcutaneously. The horse will be monitored for any abnormal reactions for 4 h continuously. The horse will be checked for pain and swelling at the site of injection. If the animal shows abnormal reactions such as sweating, high fever, cough, seizure or difficulty in breathing, it will be treated symptomatically. After 4 h, it will be observed once every hour until 8 h. The horse will be housed in the stall for 3 days. If everything is normal, the horse will be released back to the pasture. The remaining two horses will be treated and monitored similarly and released after 3 day if everything goes well. Blood (10 ml) will be collected weekly from each horse. Any horse reacting to the antibody will be treated with analgesics, corticosteroids and hot packs while in the stall.

The remaining three horses will be given Peptide-1/KLH and adjuvant subcutaneously at a dose of 0.1 mg/kg, the same composition and dose used for foals as described above. In foals, this dose induced antibody production and did not produce severe reactions. Blood (10 ml) will be collected before the injection (for control value). After the peptide injection, 10 ml blood will be collected every $7^{th}$ day for the RAO season to determine antibody titer. Peptide injection will be performed in a stall, and the horses will be closely monitored for 3 days. If everything goes well with the horses, they will be released to the pasture. Their ability to resist RAO will be weekly observed during the period.

Analysis of Results:

The data will be analyzed for statistical difference between the groups and between the treated and untreated horse using a two-tailed repeated ANOVA for the titer values. If the significance is indicated, a post-hoc analysis will be performed using Tukey's test. Significance will be set at a "p" value of <0.05 for all tests. It is expected that the horses given either Peptide-1 or its antibodies will have fewer symptoms and less severe symptoms of RAO during the RAO season.

Example 8

Vaccination of Guinea Pigs with Peptide-1

We believe that other mammals can be treated with Peptide-1 or its antibodies to decrease the symptoms of asthma, including humans. Guinea pigs, a common animal model for human asthma, will be used. Guinea pigs will be vaccinated with Peptide-1 to see if Peptide-1 can help protect guinea pigs from getting asthma (experimentally induced asthma). This study will determine the antibody levels in guinea pigs injected twice (an initial injection and a 4-week booster injection) with Peptide-1 at a dose of 0.1 mg/kg subcutaneously, will determine the effectiveness of antibodies to Peptide-1 in protecting guinea pigs from experimentally induced asthma, and will determine the protection of guinea pigs from experimentally induced asthma by vaccination with Peptide-1.

Description of Investigation:

Following approval from the IACUC, this study will be performed in 3 groups of healthy guinea pigs (10 guinea pigs in each group). In group #1, guinea pigs will be injected with Peptide-1/KLH and adjuvant initially and then again 4 weeks later (the booster injection). Blood (2 ml) will be drawn from the jugular vein to determine antibody titer. Blood samples will be collected before the initial injection of the peptide, and then once every week for two months. The blood samples will be used to determine the level of antibody titer. If the guinea pigs have sufficient level of antibody, they will be used for antibody extraction.

The second group of guinea pigs will be used for injecting antibodies to Peptide-1 at a dose of 1 mg/kg body weight. These animals will be observed for asthma signs. It is expected that the asthma signs from experimentally induced asthma will be reduced from the injection of the antibodies. The third group will be used to vaccinate with the peptide (first injection and booster injections). This group will be tested for protection from the experimental asthma as did with the second group.

Experimental Induction of Asthma:

Asthma will be induced in guinea pigs by a method previously described (16). Healthy Guinea pigs will be procured from a USDA licensed dealer and housed in a regulated animal facility. Animals will be weighed and prepared for sterile injection of ovalbumin. Blood (2 ml) will be collected from the jugular vein.

The animals will be sensitized by an intraperitoneal injection of ovalbumin at a dose of 100 mg/Kg body weight. The sensitized animals will be housed in separate cages and continuously observed for any clinical, physiological or behavioral alterations. On the $10^{th}$ day after injection, the animals will be weighed. Then the animals will be challenged with ovalbumin at a lower dose of 100 ug/kg body weight (challenging dose) intraperitoneally (25). In sensitized animals, this challenging dose will cause an asthmatic response such as difficulty in breathing, increased effort to exhale air, gasping for air, rough coat, and curving of body. If administration of Peptide-1 can produce antibodies (active immunotherapy) or of antibodies to Peptide-1 (passive immunotherapy) can prevent guinea pigs from developing asthma signs, it will support the therapeutic use for asthma in mammals of the peptide or the antibody to the Peptide, including use in humans.

Blood Collection:

Blood (2 ml) will be collected from jugular vein from guinea pigs sedated with barbiturates.

Antibody Extraction:

Total IgG antibody from hyper-immune sera collected from guinea pigs will be purified by Protein-A/G affinity chromatography, by established procedures (2). Briefly, IgG from sera will be allowed to bind to Protein-A/G conjugated agarose beads in a chromatography column. After washing off all unbound serum proteins, Protein-A/G bound IgG will be eluted out by lowering pH to 2.5. Antibodies will stored in −80° C.

Antibody Titer Determination by ELISA:

Relative antibody titer will be determined by sandwich ELISA by a previously described method (17), and as described above. Briefly, ELISA plate will be coated with peptide. Serial 10-fold dilutions of sera up to 100,000 will be used as sample. After washing all unbound proteins, the amount of bound IgG specific to the peptide, will be determined by a secondary antibody, peroxidase-conjugated goat anti-guinea pig IgG (17).

Analysis of Results:

The data will be analyzed for statistical difference between the experimental groups and the control group using a two-tailed repeated ANOVA for the titer values. If the significance is indicated, a post-hoc analysis will be performed using Tukey's test. Significance will be set at a "p" value of <0.05 for all tests.

REFERENCES

1. Ainsworth D. M., Appleton J. A., Antczak D. F., Santiago M. A., Aviza G. IgG antibody responses to an inhaled antigen in horses with "heaves" (recurrent airway obstruction). Vet Immunol. Immunopathol. 84(3-4):169-80 (2002 Jan. 15).
2. Akerstrom B., Bjorck L. (1986) A physicochemical study of protein G, a molecule with unique immunoglobulin G-binding properties. J. Biol. Chem. 261:10240-7.
3. Barnes P. J., Chung K. F., Page C. P. Inflammatory mediators of asthma. Pharmacol. Rev., 40(1):49-84 (1988).
4. Beadle R. E. Summer pasture-associated obstructive pulmonary disease. In: Robinson N. E., ed. Current therapy in equine medicine. Philadelphia: W.B. Saunders Co., 512-516 (1983).
5. Bochner B. S., Busse W. W. Allergy and Asthma. J. Allergy Clin. Immunol., 115(5): 953-59 (2005).
6. Bowles K. S., Beadle R. E., Mouch S., Pourciau S. S., Littlefield-Chabaud M. A., Le Blanc C., Mistric L., Fermaglich D., Horohov D. W. A novel model for equine recurrent airway obstruction. Vet. Immunol. Immunopathol. 87(3-4):385-9 (2002).
7. Buechner-Maxwell V. Airway hyperresponsiveness. Equine respiratory disorders. The Compendium; 15:1379-1389 (1993).
8. Bureau F., Delhalle S., Bonizzi G., Fievez L., Dogne S., Kirschvink N., Vanderplasschen A., Merville M. P., Bours V., Lekeux P. Mechanism of persistent NF-Kappa B activity in the bronchi of an animal model of human asthma. J. Immunol., 165(10): 5822-5830 (2000).
9. Carlsson H. E., Lindberg A. A., Hammarström S. Titration of antibodies to salmonella O. antigens by enzyme-linked immunosorbent assay. Infect. Immun. 6(5):703-8 (1972).
10. Costa, L. R., Seahorn, T. L., Moore, R. M., Taylor, H. W., Oliver, J. L. and Hosgood, G. L. Correlation of clinical score, intrapleural pressure, cytologic findings of bronchoalveolar fluid, and histopathologic lesions of pulmonary tissue in horses with summer pasture-associated obstructive pulmonary disease. Am. J. Vet. Res. 61(2), 167-173 (2000).
11. Derksen F. J., Robinson, N. E. Overview of the equine respiratory system. In: Equine Respiratory Diseases, Ed. Lekeux P. International Veterinary Information Service (www.ivis.org), Ithaca, N.Y., USA, 2002.
12. Drazen J. M., Finn P. W., DeSanctis G. T. Mouse models of airway responsiveness. In: Annual Review of Physiology. Hoffman J. F., De Weer P. (eds). Annual Reviews, Inc., California, 61: 593-625 (1999).
13. Drazen J. M. Introduction to mediators of inflammation. Leff A(ed). In: Pulmonary and Critical Care Pharmacology and Therapeutics. McGraw-Hill, New York, 119-123 (1996).
14. Drazen J. M. Physiologic basis and interpretation of common indices of respiratory mechanical function. Environ. Health Prespective, 16: 11-16 (1976).
15. Drazen J. M, Takebayashi T., Long N. C., DeSanctis G. T., Shore S. A. Animal models of asthma and chronic bronchitis. Clin. Experiment. Allergy, 29: 37-47 (1999).
16. Drazen J. M, Venugopal C. S., Soter N. A. H2 receptor mediated inhibition of immediate type hypersensitivity reactions in vivo. Am. Rev. Respir. Dis., 117: 479-484 (1978).
17. Garland S. M., Locarnini S. A., Gust I. D. A solid-phase enzyme-linked immunosorbent assay (ELSIA) for detection of antibody to rubella virus. Pathology. 11:393-9 (1979).
18. Harada M., Magara-Koyanagi K., Watarai H., Nagata Y., Ishii Y., Kojo S., Horiguchi S., Okamoto Y., Nakayama T., Suzuki N., Yeh W. C., Akira S., Kitamura H., Ohara O., Seino K., Taniguchi M. IL-21-induced Bepsilon cell apoptosis mediated by natural killer T cells suppresses IgE responses. J. Exp. Med.; 203(13):2929-37 (2006).
19. Hargreave F. E., Dolovich J., O'Bryne M. B., et al., The origin of airway hyperresponsiveness. J. Allergy. Clin. Immunol., 78: 825-829 (1986).
20. Hart L. A., Krishnan V. L, Adcock I. M., Barnes P. J., Chung K. F. Activation and localization of transcription factor, nuclear factor Kappa B, in asthma. Am. Rev. Respir. Crit. Care Med., 158: 1585-1590 (1998).
21. Hjelm H., Hjelm K., Sjöquist J. Protein A from *Staphylococcus aureus*. Its isolation by affinity chromatography and its use as an immunosorbent for isolation of immunoglobulins. FEBS Lett. 28(1):73-6 (1972).
22. Horohov D. W., Beadle R. E., Mouch S., Pourciau S. S. Temporal regulation of cytokine mRNA expression in equine recurrent airway obstruction. 108 (1-2):237-45 (2005).
23. Johansson S., Andersson K., Wennergren G., Wennerås C., Rudin A. CC16 inhibits the migration of eosinophils towards the formyl peptide fMLF but not towards PGD2. Inflammation. 32(2):65-9 (2009).
24. Katavolos P., Ackerley C. A., Viel L., Clark M. E., Wen X. AND Bienzle D. Clara Cell Secretary Protein Is Reduced in Equine Recurrent Airway Obstruction. Vet. Pathol. 46:604-613 (2009).
25. Krishnakumar S., Holmes E. P., Moore R. M., Kappel L., Venugopal C. S. Non-adrenergic, non-cholinergic excitatory innervation in asthma: Role of neurokinin-2 receptors. J. Auton. & Autacoid. Pharmacol., 22: 1-11 (2002).
26. Lee H. A., Kwon B., Hur G. Y., Choi S. J., Nahm D. H, Park H. S. Isotype and IgG subclass distribution of autoantibody response to alpha-enolase protein in adult patients with severe asthma. Yonsei Med. J.; 49(6):923-30 (2008).
27. McGinnis S, Madden T. L. BLAST: at the core of a powerful and diverse set of sequence analysis tools. Nucleic Acids Res. 1; 32 (Web Server issue):W20-5 (2004).
28. Morán G., Folch H., Araya O., Burgos R., Barria M. Detection of reaginic antibodies against *Faenia rectivirgula* from the serum of horses affected with Recurrent Airway Obstruction by an in vitro bioassay, Vet. Res. Commun., 34(8):719-26 (2010).
29. K. Radon. The two sides of the "Endotoxin Coin". Occup. Environ. Med.; 63:73-78 (2006)
30. Roy, S. R. Asthma. South. Med. J., 96(11):1061-67 (2003).
31. Seahorn T L, Beadle R E, McGorum B C, Marley C L. Quantification of antigen-specific antibody concentrations in tracheal lavage fluid of horses with summer pasture-associated obstructive pulmonary disease. Am. J. Vet. Res.; 58: 1408-1411 (1997).
32. Schmitz N., Dietmeier K., Bauer M., Maudrich M., Utzinger S., Muntwiler S., Saudan P., Bachmann M. F. Displaying Fel. d1 on virus-like particles prevents reactogenicity despite greatly enhanced immunogenicity: a novel therapy for cat allergy. J. Exp. Med.; 206(9):1941-55 (2009).
33. Snapper J. R. Large animal models of asthma. Am. Rev. Respir. Dis., 133: 351-352, (1986).
34. Venugopal C. S., Mendes, L. C. N., Peiro, J. R., Laborde, S., Stokes, A. M., Moore, R. M. Transcriptional changes associated with equine recurrent airway obstruction in affected and unaffected horses. Am. J. Vet. Res., 71(4): 476-82 (2010).

35. Westritschnig K., Linhart B., Focke-Tejkl M., Pavkov T., Keller W., Ball T., Mari A., Hartl A., Stöcklinger A., Scheiblhofer S., Thalhamer J., Ferreira F., Vieths S., Vogel L., Böhm A., Valent P., Valenta R. A hypoallergenic vaccine obtained by tail-to-headrestructuring of timothy grass pollen profilin, Phl p 12, for the treatment of cross-sensitization to profilin. J Immunol. 179(11):7624-34 (2007).
36. Xia Y. C., Schuliga M., Shepherd M., Powell M., Harris T., Lagenbach S. Y., Tan P. S., Gerthoffer W. T., Hogarth P. M., Stewart A. G., Mackay G. A. Functional Expression of IgG-Fc Receptors in Human Airway Smooth Muscle Cells. Am. J. Respir. Cell Mol. Biol. (2010).
37. Yasuda, Y., Yoko Matsumura, Kazuki Kasahara, Noriko Ouji, Shigeki Sugiura, Keiichi Mikasa, and Eiji Kita. Microbial exposure early in life regulates airway inflammation in mice after infection with Streptococcus pneumoniae with enhancement of local resistance. Am. J. Physiol. Lung Cell Mol. Physiol. 298(1):L67-78 (2010).

The complete disclosures of all references cited in this application are hereby incorporated by reference. In the event of an otherwise irreconcilable conflict, however, the present specification shall control.

What is claimed:

1. A pharmaceutical composition for treating mammalian respiratory disorders comprising SEQ ID NO:1 linked to an immunogenic protein carrier, and at least one pharmaceutically acceptable excipient,
    wherein said SEQ ID NO:1 linked to the immunogenic protein carrier is not human CC10 or horse CC10, and
    wherein said immunogenic protein carrier increases recognition of SEQ ID NO:1 by lymphocytes to increase antibody production.

2. The pharmaceutical composition of claim 1, wherein the SEQ ID NO:1 is covalently or non-covalently linked to the immunogenic protein carrier.

3. The pharmaceutical composition of claim 2, wherein the immunogenic protein carrier is keyhole limpet hemocyanin.

4. The pharmaceutical composition of claim 1, wherein the at least one pharmaceutically acceptable excipient is an adjuvant or other pharmaceutically acceptable compound.

5. The pharmaceutical composition of claim 4, wherein the adjuvant is incomplete Freund's adjuvant.

6. A method to treat a respiratory allergic disease in a mammal, said method comprising administering to the mammal a therapeutically effective amount of the pharmaceutical composition of claim 1.

7. The method of claim 6, wherein the mammal is a horse.

8. The method of claim 6, wherein the mammal is a human.

9. A method to detect mammals that are susceptible to respiratory airway disease, said method comprising contacting serum from said mammal to a peptide consisting of SEQ ID NO:1; and measuring the levels of antibody to CC10 in the serum;
    wherein the level of antibodies bound to said peptide is indicative of respiratory airway disease.

10. The method of claim 9, wherein the mammal is a horse.

11. The method of claim 9, wherein the mammal is a human.

12. A pharmaceutical composition for treating mammalian respiratory disorders comprising a peptide consisting of SEQ ID NO:1 and at least one pharmaceutically acceptable excipient.

13. The pharmaceutical composition of claim 12, wherein the at least one pharmaceutically acceptable excipient is an adjuvant or other pharmaceutically acceptable compound.

14. The pharmaceutical composition of claim 12, wherein the adjuvant is incomplete Freund's adjuvant.

15. A method to treat a respiratory allergic disease in a mammal, said method comprising administering to the mammal a therapeutically effective amount of the pharmaceutical composition of claim 12.

16. The method of claim 12, wherein the mammal is a horse.

17. The method of claim 12, wherein the mammal is a human.

\* \* \* \* \*